(12) United States Patent
Takahashi et al.

(10) Patent No.: US 11,998,559 B2
(45) Date of Patent: *Jun. 4, 2024

(54) AGENT FOR PREVENTING OR AMELIORATING ALZHEIMER'S DISEASE

(71) Applicant: DAICEL CORPORATION, Osaka (JP)

(72) Inventors: Kaori Takahashi, Tokyo (JP); Katsuyuki Mukai, Tokyo (JP); Yasuyuki Igarashi, Tokyo (JP); Kohei Yuyama, Sapporo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/756,978

(22) PCT Filed: Oct. 3, 2018

(86) PCT No.: PCT/JP2018/037018
§ 371 (c)(1),
(2) Date: Apr. 17, 2020

(87) PCT Pub. No.: WO2019/078005
PCT Pub. Date: Apr. 25, 2019

(65) Prior Publication Data
US 2021/0121490 A1    Apr. 29, 2021

(30) Foreign Application Priority Data
Oct. 18, 2017    (JP) ................. 2017-201880

(51) Int. Cl.
*A61K 31/7032*    (2006.01)
*A61P 25/28*    (2006.01)

(52) U.S. Cl.
CPC .......... *A61K 31/7032* (2013.01); *A61P 25/28* (2018.01)

(58) Field of Classification Search
CPC .................. A61P 25/28; A61K 31/7004–7032
See application file for complete search history.

(56) References Cited

U.S. PATENT DOCUMENTS

| 2007/0275908 A1 | 11/2007 | Defrees et al. |
| 2010/0028465 A1 | 2/2010 | Fukami |
| 2012/0264928 A1 | 10/2012 | Noguchi et al. |
| 2019/0254992 A1* | 8/2019 | Arkadir ............... A61P 25/16 |
| 2021/0177778 A1 | 6/2021 | Mukai et al. |

FOREIGN PATENT DOCUMENTS

| JP | 8-113535 A | 5/1996 |
| JP | 2011-195531 A | 10/2011 |
| JP | 2014-224132 A | 12/2014 |
| JP | 2016-145175 A | 8/2016 |
| JP | 6981619 B2 | 12/2021 |
| KR | 10-2018-0091223 A | 8/2018 |
| WO | WO 2008/087704 A1 | 7/2008 |
| WO | WO 2018/212250 A1 | 11/2018 |

OTHER PUBLICATIONS

Hiroyuki, Fukami, English machine translation of WO2008/087704, 12 pages (Year: 2008).*
Lee, Y. et al., Evidence-Based COmplementary and Alternative Medicine, "Administration of Glucosylceramide Ameliorated the Memory Impairment in Aged Mice", 2013, 10 pages (Year: 2013).*
Uchiyama, T. et al., Journal of Health Science, "Oral Intake of Glucosylceramide Improves Relatively Higher Level of Transepidermal Water Loss in Mice and Healthy Human Subjects", 2008, vol. 54, No. 5, pp. 559-566 (Year: 2008).*
Capucho, P. et al., Dement Neuropsychol, "Judgement in Mild Cognitive Impairment and Alzheimer's disease", 2011, vol. 5, No. 4, pp. 297-302 (Year: 2011).*
Goodman, Y. and M. P. Mattson, "Ceramide Protects Hippocampal Neurons Against Excitotoxic and Oxidative Insults, and Amyloid β-Peptide Toxicity," J. Neurochem. (1996), vol. 66, pp. 869-872.
Igarashi, Y., "Creation of functional material containing agricultural and forestry product-derived ceramide," Journal of Agricultural and Food Technology (2016), vol. 12, No. 1, pp. 21-24.
International Search Report dated Jan. 8, 2019, in PCT/JP2018/037018.
Mukai, K., "Functionality of konjac potato-derived ceramide as food material," Bio Industry (2002), vol. 19, No. 8, pp. 16-26.
Takahashi et al., "Preventive effects of dietary konjak ceramide on the Alzheimer's brain," Proceedings from the Annual Meeting 2018 Nagoya of Japan Society for Bioscience, Biotechnology, and Agrochemistry (Mar. 2018), 3 pages.
Written Opinion of the International Searching Authority dated Jan. 8, 2019, in PCT/JP2018/037018.
Yuyama et al., "Sphingolipid-modulated Exosome Secretion Promotes Clearance of Amyloid-β by Microglia," J. Biol. Chem. (2012), vol. 287, No. 14, pp. 10977-10989.
Costantini et al., "Ceramide and Cholesterol: Possible Connections Between Normal Aging of the Brain and Alzheimer's Disease. Just hypotheses or molecular pathways to be identified?," Alzheimer's & Dementia, vol. 1, 2005, pp. 43-50.

(Continued)

*Primary Examiner* — Bahar Craigo
(74) *Attorney, Agent, or Firm* — Birch, Stewart, Kolasch & Birch, LLP (57) ABSTRACT

The purpose of the present invention is to provide an agent for preventing or ameliorating Alzheimer's disease, said agent being able to effectively suppress the accumulation of amyloid β proteins using a safe material, which has been used in foods for many years, and improve spontaneous alternation behavior change ratio. Ceramides (in particular, a glucosylceramide originating in *Amorphophallus konjac*) can effectively suppress the accumulation of amyloid β proteins and thus enables the prevention or amelioration of Alzheimers disease.

7 Claims, 3 Drawing Sheets

(56) References Cited

OTHER PUBLICATIONS

Extended European Search Report for European Application No. 18868138.1, dated Jul. 1, 2021.

* cited by examiner

AGENT FOR PREVENTING OR AMELIORATING ALZHEIMER'S DISEASE

TECHNICAL FIELD

The present invention relates to an agent for preventing or ameliorating Alzheimer's disease, which can effectively suppress the accumulation of amyloid β protein (Aβ) in the brain. In addition, the present invention relates to an agent for maintaining or ameliorating memory which is able to suppress decrease in memory or ameliorate decreased memory caused by the accumulation of Aβ, an agent for maintaining or ameliorating judgment which is able to suppress decrease in judgment or ameliorate decreased judgment caused thereby, and an agent for maintaining or ameliorating a cognitive function which is able to suppress decrease in cognitive function or ameliorate decreased cognitive function caused thereby.

BACKGROUND ART

Alzheimer's disease is a progressive neurodegenerative disease that results from neuronal cell death or synaptic dysfunction. Pathological features of Alzheimer's disease include accumulation of abnormal structures such as senile plaques and neurofibrillary tangles in the brain. At present, dementia is said to be caused by Alzheimers disease in most cases, and early establishment of measures for preventing or treating Alzheimer's disease is desired.

Alzheimer's disease can be classified into familial Alzheimer's disease and sporadic Alzheimer's disease. Familial Alzheimer's disease is thought to be caused by mutations in genes such as the APP gene, the presenilin-1 gene and the presenilin-2 gene, and develops in relative youth. However, familial Alzheimer's disease accounts for only about 1% of all Alzheimer's disease patients, and most of them suffer from sporadic Alzheimer's disease. While ApoE isoform 4 is known as a risk factor for sporadic Alzheimer's disease, aging is the largest risk factor, and everyone has the potential to develop Alzheimer's disease.

Alzheimer's disease is thought to develop due to the accumulation of Aβ in the brain for many years. In order to prevent Alzheimer's disease, it is important to continuously suppress Aβ even before symptoms such as dementia appear. Therefore, an agent for preventing Alzheimer's disease is required not only to have an effect of suppressing the accumulation of Aβ, but also to be safe even when taken continuously for many years. Ingredients contained in food materials, which have been used in foods for many years, are considered safe even when taken continuously over a long period of time. However, at present, no sufficient study has been made yet on those which have been used in foods for many years and can effectively suppress the accumulation of Aβ.

Agents for suppressing the accumulation of Aβ have been extensively researched. For example, Patent Document 1 discloses an amyloid fibril formation inhibitor containing a water-soluble peptide metal complex array. Further, for example, Patent Document 2 discloses an inhibitor for inhibiting the aggregation of Aβ caused by a mutation in the GNE gene, containing at least any one of N-acetylneuraminic acid, N-acetylmannosamine and sialyl lactose.

PRIOR ART DOCUMENTS

Patent Documents

Patent Document 1: JP 2016-145175 A
Patent Document 2: JP 2014-224132 A

SUMMARY OF THE INVENTION

Problems to be Solved by the Invention

An object of the present invention is to provide an agent for preventing or ameliorating Alzheimer's disease, which can effectively suppress the accumulation of Aβ using a safe material that has been used in foods. In addition, another object of the present invention is to provide an agent for maintaining or ameliorating memory which is able to suppress decrease in memory or ameliorate decreased memory, an agent for maintaining or ameliorating judgment which is able to suppress decrease in judgment, and an agent for maintaining or ameliorating a cognitive function which is able to suppress decrease in cognitive function or ameliorate decreased cognitive function, using a safe material that has been used in foods.

Means for Solving the Problem

The present inventors have made intensive studies to solve the above-described problems, and found that ceramides (in particular, glucosylceramide derived from tuber of *Amorphophallus konjac*) effectively suppress the accumulation of Aβ and have an effect of suppressing decrease in cognitive function, an effect of maintaining memory, an effect of maintaining judgment, and the like. In other words, the present inventors have found that Alzheimer's disease can be prevented or ameliorated by continuous intake of a ceramide. The present invention has been completed as a result of further studies based on such findings.

The present invention relates to uses for preventing and ameliorating Alzheimer's disease, and provides the following aspects of the invention.

1-1. An agent for preventing or ameliorating Alzheimer's disease, containing a ceramide as an active ingredient.

1-2. The agent for preventing or ameliorating Alzheimer's disease according to 1-1, wherein the ceramide is derived from tuber of *Amorphophallus konjac*.

1-3. The agent for preventing or ameliorating Alzheimer's disease according to 1-1 or 1-2, wherein the ceramide is glucosylceramide.

1-4. The agent for preventing or ameliorating Alzheimer's disease according to any one of 1-1 to 1-3, which is a food or beverage for preventing Alzheimer's disease.

1-5. The agent for preventing or ameliorating Alzheimer's disease according to any one of 1-1 to 1-3, which is a pharmaceutical for preventing Alzheimer's disease.

1-6. Use of a ceramide for the manufacture of an agent for preventing or ameliorating Alzheimer's disease.

1-7. The use according to 1-6, wherein the ceramide is derived from tuber of *Amorphophallus konjac*.

1-8. The use according to 1-6 or 1-7, wherein the ceramide is glucosylceramide.

1-9. The use according to any one of 1-6 to 1-8, wherein the agent for preventing or ameliorating Alzheimer's disease is a food or beverage.

1-10. The use according to any one of 1-6 to 1-8, wherein the agent for preventing or ameliorating Alzheimer's disease is a pharmaceutical.

1-11. A ceramide for use in treatment for preventing or ameliorating Alzheimer's disease.

1-12. The ceramide according to 1-11, wherein the ceramide is derived from tuber of *Amorphophallus konjac*.

1-13. The ceramide according to 1-11 or 1-12, wherein the ceramide is glucosylceramide.

1-14. A method for preventing or ameliorating Alzheimer's disease, including the step of administering an effective amount of a ceramide to a person in need of prevention or amelioration of Alzheimer's disease.

1-15. The method for preventing or ameliorating Alzheimer's disease according to 1-14, wherein the ceramide is derived from tuber of *Amorphophallus konjac*.

1-16. The method for preventing or ameliorating Alzheimer's disease according to 1-14 or 1-15, wherein the ceramide is glucosylceramide.

The present invention also relates to uses for maintaining or ameliorating memory, and provides the following aspects of the invention.

2-1. An agent for maintaining or ameliorating memory, containing a ceramide as an active ingredient.

2-2. The agent for maintaining or ameliorating memory according to 2-1, wherein the ceramide is derived from tuber of *Amorphophallus konjac*.

2-3. The agent for maintaining or ameliorating memory according to 2-1 or 2-2, wherein the ceramide is glucosylceramide.

2-4. The agent for maintaining or ameliorating memory according to any of 2-1 to 2-3, which is a food or beverage for maintaining or ameliorating memory.

2-5. The agent for maintaining or ameliorating memory according to any one of 2-1 to 2-3, which is a pharmaceutical for maintaining or ameliorating memory.

2-6. Use of a ceramide for the manufacture of an agent for maintaining or ameliorating memory.

2-7. The use according to 2-6, wherein the ceramide is derived from tuber of *Amorphophallus konjac*.

2-8. The use according to 2-6 or 2-7, wherein the ceramide is glucosylceramide.

2-9. The use according to any one of 2-6 to 2-8, wherein the agent for maintaining or ameliorating memory is a food or beverage.

2-10. The use according to any one of 2-6 to 2-8, wherein the agent for maintaining or ameliorating memory is a pharmaceutical.

2-11. A ceramide for use in treatment for preventing or ameliorating memory.

2-12. The ceramide according to 2-11, wherein the ceramide is derived from tuber of *Amorphophallus konjac*.

2-13. The ceramide according to 2-11 or 2-12, wherein the ceramide is glucosylceramide.

2-14. A method for maintaining or ameliorating memory, including the step of administering an effective amount of a ceramide to a person in need of suppression of decrease in memory or amelioration of memory.

2-15. The method for maintaining or ameliorating memory according to 2-14, wherein the ceramide is derived from tuber of *Amorphophallus konjac*.

2-16. The method for maintaining or ameliorating memory according to 2-14 or 2-15, wherein the ceramide is glucosylceramide.

In addition, the present invention relates to uses for maintaining or ameliorating judgment, and provides the following aspects of the invention.

3-1. An agent for maintaining or ameliorating judgment, containing a ceramide as an active ingredient.

3-2. The agent for maintaining or ameliorating judgment according to 3-1 wherein the ceramide is derived from tuber of *Amorphophallus konjac*.

3-3. The agent for maintaining or ameliorating judgment according to 3-1 or 3-2, wherein the ceramide is glucosylceramide.

3-4. The agent for maintaining or ameliorating judgment according to any one of 3-1 to 3-3, which is a food or beverage for maintaining or ameliorating judgment.

3-5. The agent for maintaining or ameliorating judgment according to any one of 3-1 to 3-3, which is a pharmaceutical for maintaining or ameliorating judgment.

3-6. Use of a ceramide for the manufacture of an agent for maintaining or ameliorating judgment.

3-7. The use according to 3-6, wherein the ceramide is derived from tuber of *Amorphophallus konyaj*.

3-8. The use according to 3-6 or 3-7, wherein the ceramide is glucosylceramide.

3-9. The use according to any one of 3-6 to 3-8, wherein the agent for maintaining or ameliorating judgment is a food or beverage.

3-10. The use according to any one of 3-6 to 3-8, wherein the agent for maintaining or ameliorating judgment is a pharmaceutical.

3-11. A ceramide for use in treatment for maintaining or ameliorating judgment.

3-12. The ceramide according to 3-11, wherein the ceramide is derived from tuber of *Amorphophallus konjac*.

3-13. The ceramide according to 3-11 or 3-12, wherein the ceramide is glucosylceramide.

3-14. A method for maintaining or ameliorating judgment, including the step of administering an effective amount of a ceramide to a person in need of suppression of decrease in judgment or in need of amelioration of judgment.

3-15. The method for maintaining or ameliorating judgment according to 3-14, wherein the ceramide is derived from tuber of *Amorphophallus konjac*.

3-16. The method for maintaining or ameliorating judgment according to 3-14 or 3-15, wherein the ceramide is glucosylceramide.

The present invention also relates to uses for maintaining or ameliorating a cognitive function, and provides the following aspects of the invention.

4-1. An agent for maintaining or ameliorating a cognitive function, containing a ceramide as an active ingredient.

4-2. The agent for maintaining or ameliorating a cognitive function according to 4-1, wherein the ceramide is derived from tuber of *Amorphophallus konjac*.

4-3. The agent for maintaining or ameliorating a cognitive function according to 4-1 or 4-2, wherein the ceramide is glucosylceramide.

4-4. The agent for maintaining or ameliorating a cognitive function according to any one of 4-1 to 4-3, which is a food or beverage for maintaining or ameliorating a cognitive function.

4-5. The agent for maintaining or ameliorating a cognitive function according to any one of 4-1 to 4-3, which is a pharmaceutical for maintaining or ameliorating a cognitive function.

4-6. Use of a ceramide for the manufacture of an agent for maintaining or ameliorating a cognitive function.

4-7. The use according to 4-6, wherein the ceramide is derived from tuber of *Amorphophallus konjac*.

4-8. The use according to 4-6 or 4-7, wherein the ceramide is glucosylceramide.

4-9. The use according to any one of 4-6 to 4-8, wherein the agent for maintaining or ameliorating a cognitive function is a food or beverage.

4-10. The use according to any one of 4-6 to 4-8, wherein the agent for maintaining or ameliorating a cognitive function is a pharmaceutical.

4-11. A ceramide for use in treatment for maintaining or ameliorating a cognitive function.

4-12. The ceramide according to 4-11, wherein the ceramide is derived from tuber of *Amorphophallus konjac*.

4-13. The ceramide according to 4-11 or 4-12, wherein the ceramide is glucosylceramide.

4-14. A method for maintaining or ameliorating a cognitive function, including the step of administering an effective amount of a ceramide to a person in need of suppression of decrease in cognitive function or amelioration of a cognitive function.

4-15. The method for maintaining or ameliorating a cognitive function according to 4-14, wherein the ceramide is derived from tuber of *Amorphophallus konjac*.

4-16. The method for maintaining or ameliorating a cognitive function according to 4-14 or 4-15, wherein the ceramide is glucosylceramide.

Advantages of the Invention

The agent for preventing or ameliorating Alzheimers disease according to the present invention can effectively suppress the accumulation of Aβ in the brain, and thus can prevent the onset of Alzheimers disease and ameliorate symptoms thereof. Furthermore, the agent for preventing or ameliorating Alzheimer's disease according to the present invention can also ameliorate behavior disorder. In addition, in order to prevent Alzheimer's disease, it is necessary to continuously take an active ingredient that suppresses the accumulation of Aβ. In this regard, the agent for preventing or ameliorating Alzheimer's disease according to the present invention contains a ceramide that has been used in foods for a long time, is highly safe and has no concern about side effects, and thus can be continuously taken for many years, which is required for preventing Alzheimer's disease.

Further, the present invention can provide an agent for maintaining or ameliorating memory which is able to suppress decrease in memory or ameliorate decreased memory caused by the accumulation of Aβ, an agent for maintaining or ameliorating judgment which is able to suppress decrease in judgment or ameliorate decreased judgment caused thereby, and an agent for maintaining or ameliorating a cognitive function which is able to suppress decrease in cognitive function or ameliorate decreased cognitive function caused thereby.

EMBODIMENTS OF THE INVENTION

1. Agent for Preventing or Ameliorating Alzheimer's Disease

The agent for preventing or ameliorating Alzheimer's disease according to the present invention is characterized by containing a ceramide as an active ingredient. Hereinafter, the agent for preventing or ameliorating Alzheimer's disease according to the present invention will be described in detail.

[Active Ingredient]

The agent for preventing or ameliorating Alzheimer's disease according to the present invention contains a ceramide as an active ingredient.

Ceramides are compounds having a structure in which a fatty acid is amide-bonded to a sphingoid. Sphingoids are long-chain amino alcohols in which a hydroxyl group is bonded to at least the carbon atoms at the 1 and 3 positions and an amino group is bonded to the carbon atom at the 2 position. In the present invention, the "ceramide" encompasses also glucosylceramide in which one molecule of glucose is bonded to a ceramide skeleton wherein a sphingoid base and a fatty acid are amide-bonded to each other. In the agent for preventing Alzheimer's disease according to the present invention, the use of a ceramide makes it possible to suppress the accumulation of Aβ and effectively prevent Alzheimer's disease.

The ceramide used in the present invention is preferably derived from a plant. The plant from which the ceramide is derived is not particularly limited, and includes almond, sea lettuce, green laver, goosefoot, acacia, madder, red grape, red pine (including pine resin, amber and copal; the same applies to pines), agaricus, *Lactuca indica*, akebi, morning glory, azalea, hydrangea, *Angelica keiskei*, adzuki bean, asparagus, acerola, gambir, anise, avocado, licorice, *Hydrangea serrata* var. *thunbergii*, *Gynostemma pentaphyllum*, *Citrus natsudaidai*, amaryllis, marshmallow, arnica, aloe, angelica, apricot, encore, benzoin, rush, chestnut rose, yew, fig, ginkgo, *Citrus iyo*, ylang-ylang, fennel, oolong tea, turmeric, *Malva sylvestris*, self-heal, udo, Japanese apricot, *Quercus salicina*, *Citrus unshu*, rose fruit, eschalot, Siberian ginseng, common broom, enoki mushroom, elderflower, pea, orchid, golden orange, psyllium, scotch thistle, barley, *Atractylodes japonica*, osmanthus, hypericum, *Lamium album* var. *barbatun*, *Dioscorea tokoro*, olive, oregano, orange (including orange peel), carnation, cacao, Japanese persimmon, ground ivy, cocktail fruit, pueraria root, oak, *Erythronium japonicum*, pumpkin, German chamomile, camucamu, chamomile, *Trichosanthes cucumeroides*, Japanese larch, Kara Mandarin, Chinese quince, garcinia, cardamom, kawachi-bankan pomelo, kampei (a species of *Citrus reticulata*), raspberry, kiwi, balloon flower, cabbage (including kale), caraway, cucumber, *Citrus unshiu×sinensis*, kumquat, ginkgo nut, guava, matrimony vine, kudzu vine, gardenia, cumin, cranberry, walnut, grapefruit, clementine, clove, black pine black soybean, chlorella, cassia seed, cranesbill, lingberry, pepper, cosmos, burdock, wheat (including wheat germ), sesame, *Brassica chinensis* var. *komatsuna*, rice (including rice bran), coriander, konjak (tuber of *Amorphophallus konjac*) (including Konjac flying powder), kelp, salmonberry, cypress, pomegranate, sweet potato, dasheen, sugar cane, sugar beet, saffron, pomelo, hawthorn, xanthoxylum, shiitake mushroom, cyclamen, perilla, shimeji mushroom, white potato, peony, jasmine, *Coix lacryma-jobi*, garland chrysanthemum, ginger, sweet flag, *Quercus myrsinifolia*, winter daphne, cinnamon, watermelon, sweet pea, sweet spring, field horsetail, star anise, star apple, *Citrus sudachi*, stevia, plum, sage (salvia), setoka, mallow, seminole, celery, *Cnidium officinale*, *Swertia japonica*, buckwheat, fava bean, radish, soybean (including bean curd lees), sour orange, thyme, bamboo shoot, onion, tarragon, taro, *Citrus tankan*, tangor, *Salviae miltiorrhizae Radix*, tangelo, dandelion, chicory, *Oenothera tetraptera*, horsetail, camellia, camellia, camellia, centella, clover, vine, *Tetragonia tetragonoides, Farfugium japonicum*, dill, dekopon (*Citrus reticulata Siranui*), geranium, wax gourd, capsicum, *Angelica acutiloba*, caterpillar fungus, maize, *Houttuynia cordata*, ipecac, gutta-percha tree, ash, Chinese yum, shepherd's purse, natsumi (a species of citrus), Chinese citron, nutmeg, nandina, balsam pear, *Allium tuberosum*, carrot, garlic, leek, yarrow, saw palmetto, *Allium grayi*, verbena, palm, pineapple, hibiscus, chickweed, basil, parsley, rye, *Citrus hassaku*, Japanese mint, *Coix lachryma-jobi* var. *ma-yuen*, banaba, *Lagerstroemia speciosa*, vanilla, paprika, hamamelis, haruka (a species of citrus), harumi (a species of citrus), harehime (a species of citrus), *Citrus grandis*, beetroot, bell pepper, red spider lily, water chestnut, *Hizikia fusiforme*, pistachio, hyssop (*Hywsopus oficinalis*), daisy, red poppy, hinoki cypress, hinoki leaf, castor seed, sunflower, sunflower, himetsuki (a species of citrus), *Citrus tamurana*, loquat, phalaenopsis, fenugreek, *Petasites japonicus*, blackberry, plum, blueberry (including bilberry), prune, shaddock, loofah, safflower, benimadonna (a species of citrus), belladonna, bergamot, balsam, spinach, Japanese lantern plant, lime, tree peony, hop, jojoba, ponkan (*Citrus reticulata*), maitake mashroom, ephedra, maca, macadamian nut, marcot, silver vine marigold, marihime (a species of strawberry), mango, mitsuba, mineola, mimosa, mioga ginger, myrrh, gromwell, mace, melissa, melilot, melon, cotton (including cottonseed oil cake), bean sprout, cornflower, Japanese yam, golden-baded lily, sagebrrsh, eucalyptus, saxifrage, yuzu, lily, yoquinin, Aster yomena (aster), mugwort, lime, rye, lilac, raspberry, peanut, *Allium bakeri*, apple (including apple fiber), gentian, *Delosperma cooperi*, litchi, lettuce, lemon, astragalus, lotus root, rose hip, rosemary, laurier, scallion, and wasabi (including horseradish). Among these, potatoes such as tuber of *Amorphophallus konjac*, sweet potato, white potato, dasheen, Japanese yum and Chinese yam, rice and wheat are preferred, potatoes are more preferred, and tuber of *Amorphophallus konjac* is further preferred.

In the ceramide used in the present invention, the structure of the sphingoid moiety is not particularly limited, but is preferably a structure in which the bond between the carbon atoms at the 8 and 9 positions is a double bond. Specific examples of the structure of the sphingoid moiety constituting the ceramide used in the present invention include 4-hydroxy-trans-8-sphingenine, 4-hydroxy-cis-8-sphingenine, trans-8-sphingenine, cis-8-sphingienine, trans-4, trans-8-sphingadienine, and trans-4, cis-8-sphingadienine. Among these, more preferred are trans-4, cis-8-sphingadienine, trans-4-trans-8-sphingadienine, 4-hydroxy-cis-8-sphingenine, and 4-hydroxy-trans-8-sphingenine. Further preferred are trans-4, cis-8-sphingadienine and trans-4-trans-8-sphingadienine.

In the ceramide used in the present invention, the number of carbon atoms of the fatty acid bonded to the sphingoid moiety is not particularly limited, but is 2 to 30, preferably 6 to 30, more preferably 6 to 24, particularly preferably 16 to 18. The fatty acid may be any of a saturated fatty acid, an unsaturated fatty acid containing a carbon-carbon double bond and/or a carbon-carbon triple bond, and an α-hydroxy fatty acid.

Specific examples of the fatty acid bonded to the sphingoid moiety in the ceramide used in the present invention include hexanoic acid (C6:0), octanoic acid (C8:0), decanoic acid (C10:0), dodecanoic acid (C12:0), tetradecanoic acid (C14:0), hexadecanoic acid (C16:0), octadecanoic acid (C18:0), icosanoic acid (C20:0), heneicosanoic acid (C21:0), docosanoic acid (C22:0), trichosanoic acid (C23:0), tetradocosanoic acid (C24:0), pentacosanoic acid (C25:0), hexadocosanoic acid (C26:0), heptacosanoic acid (C27:0), octadocosanoic acid (28:0), and cis-9-octadecenoic acid (C18:1). In the indication "CX:Y" put in parentheses for the fatty acids, CX represents the number of carbon atoms per molecule, Y represents the number of unsaturated bonds per molecule. For example, "C16:0" represents a fatty acid having 16 carbon atoms and 0 unsaturated bonds. Among these, preferred are hexanoic acid, hexadecanoic acid, octadecanoic acid and tetracosanoic acid.

The ceramide used in the present invention is preferably an *Amorphophallus konjac*-derived ceramide, more preferably an *Amorphophallus konjac*-derived glucosylceramide.

The *Amorphophallus konjac*-derived ceramide used in the present invention may be obtained from tuber of *Amorphophallus konjac* itself, or may be obtained from konjak raw material refined powder or by-product Konjac flying powder. When an *Amorphophallus konjac*-derived ceramide is used as the active ingredient of the agent for preventing or ameliorating Alzheimer's disease according to the present invention, a ceramide obtained from Konjac flying powder is suitably used from the viewpoint of effective utilization of resources.

In the agent for preventing or ameliorating Alzheimer's disease according to the present invention, the ceramide may be a purified product or a roughly purified product, or an extract extracted from a plant material containing a ceramide.

Hereinafter, a method for producing *Amorphophallus konjac*-derived glucosylceramide (hereinafter sometimes referred to as "konjak glucosylceramide") taken as an example will be described.

Konjak glucosylceramide can be obtained by performing extraction treatment using an extraction solvent and an extraction material such as tuber of *Amorphophallus konjac*, konjak refined powder, or Konjac flying powder (hereinafter, sometimes referred to as "*Amorphophallus konjac* material").

Examples of the extraction solvent used in the extraction treatment of konjak glucosylceramide include monohydric lower alcohols such as methanol, ethanol and isopropanol; polyhydric alcohols such as 2-butanol, ethylene glycol and propylene glycol; oxygen-containing polar organic solvents such as acetone, dimethyl sulfoxide, dioxane, tetrahydrofuran and diethyl ether; nitrogen-containing polar organic solvents such as dimethylformamide and pyridine; halogen-containing polar organic solvents such as dichloromethane, chloroform and trichloroethylene; nonpolar or low-polar organic solvents such as hexane and isooctane. One of these extraction solvents may be used alone, or two or more thereof may be used in combination. Among these extraction solvents, a monohydric lower alcohol is preferred, and ethanol is further preferred, from the viewpoint of efficient extraction of konjak glucosylceramide.

In addition, water may be contained in the extraction solvent. However, as the water content of the extraction solvent increases, the extraction efficiency of konjak glucosylceramide decreases. When the water content of the extraction solvent exceeds 10% by weight, the extraction efficiency of konjak glucosylceramide significantly decreases. Especially, when the water content of the extraction solvent exceeds 15% by weight, konjak glucosylceramide is hardly extracted. Therefore, when water is contained in the extraction solvent, it is necessary to set the amount of water so as not to affect the extraction of konjak glucosylceramide.

The amount of the extraction solvent used in the extraction treatment may be set to, for example, about 1 to 30 times, preferably about 1 to 10 times the weight of the *Amorphophallus konjac* material serving as a raw material.

The temperature at the time of the extraction treatment can be appropriately set depending on the type of the extraction solvent to be used, and is for example about 0 to 80° C. preferably about 20 to 60° C.

The extraction treatment time can be appropriately set depending on the type and amount of the extraction solvent to be used, and is for example 1 to 48 hours, preferably 2 to 20 hours.

The extraction process may be performed in any of a batch operation, a semi-continuous operation, a countercurrent multi-stage contact operation, etc., and the residue after a single extraction operation may be subjected to repetitive extraction operations using new extraction solvents.

After performing the extraction treatment in this manner, solid-liquid separation is performed using a suction filtration, a filter press, a cylinder press, a decanter, a centrifuge, a filtration centrifuge, or the like, and an extract is collected. The resulting extract can be used as a konjak glucosylceramide-containing extract as it is or after being subjected to concentration, drying and the like as necessary.

Further, the extract collected after the extraction treatment is mixed with water and heated as it is or after being subjected to concentration, drying and the like as necessary, to cause phase separation into an oil phase and an aqueous phase, and the oil phase may be collected and used as a konjak glucosylceramide-containing extract. Such treatment can remove an aldehyde, so that an extract having decreased odor peculiar to tuber of *Amorphophallus konjac* can be obtained.

A purified or roughly purified product of konjak glucosylceramide can be obtained by subjecting a konjak glucosylceramide-containing extract to a purification treatment. Examples of the purification treatment include gel filtration, ion exchange treatment and activated carbon treatment.

[Other Additive Components]

The agent for preventing or ameliorating Alzheimer's disease according to the present invention may contain, in addition to the above-mentioned ceramide, other additive components depending on the dosage form, as long as the effects of the present invention are not impaired. Examples of the additive components that can be contained in the agent for preventing Alzheimer's disease according to the present invention include water, oils and fats, waxes, hydrocarbons, fatty acids, higher alcohols, esters, plant extracts, water-soluble polymers, surfactants, metal soaps, alcohols, polyhydric alcohols, pH adjusters, antioxidants, ultraviolet absorbers, preservatives, fragrances, powders, thickeners, pigments, and chelating agents and the like. These additive components may be used alone, or two or more thereof may be used in combination. In addition, the contents of these additive components are appropriately set depending on the types of the additive components to be used, the dosage form of the agent for preventing or ameliorating Alzheimer's disease, and the like.

[Dosage Form/Formulation/Use]

The dosage form of the agent for preventing or ameliorating Alzheimer's disease according to the present invention is not particularly limited, may be any of solid, semi-solid and liquid, and may be appropriately set depending on the type, use, administration method and the like of the agent for preventing or ameliorating Alzheimer's disease.

The method of administering the agent for preventing or ameliorating Alzheimers disease according to the present invention is not particularly limited, and can be appropriately selected depending on the type of the disease to which the method is to be applied, and may be systemic or local administration. Specific examples of the method include oral, intravascular (intraarterial or intravenous), transdermal, enteral, pulmonary, and intranasal administrations. Intravascular administration also includes intravascular injections and continuous infusions. Among these, oral administration (oral ingestion), intravascular administration and intranasal administration are preferred from the viewpoint of easy administration and more effective Alzheimer's disease prevention/amelioration.

The formulation of the agent for preventing or ameliorating Alzheimer's disease according to the present invention is not particularly limited, and can be appropriately set to a formulation suitable for an administration method. Examples of the formulation include tablets, capsules, granules, powders, syrups, injections, drops and suppositories. For example, when the administration form of the agent for preventing or ameliorating Alzheimer's disease according to the present invention is oral administration (oral ingestion), the formulation is not particularly limited as long as oral administration is possible. Specific examples of the formulation include foods and beverages and pharmaceuticals for internal use.

When the agent for preventing or ameliorating Alzheimer's disease according to the present invention is used in the formulation of a food or beverage (i.e., when provided as a food or beverage for preventing or ameliorating Alzheimer's disease), the agent for preventing or ameliorating Alzheimer's disease according to the present invention may be used as it is or combined with any other food material or additive component to prepare a desired form. Examples of such foods and beverages include general foods and beverages, as well as foods for specified health use, nutritional supplements, functional foods, and foods for the sick. The form of the food or beverage is not particularly limited, and specific examples thereof include supplements such as capsules (soft capsules and hard capsules), tablets, granules, powders, jellies and liposome preparations; beverages such as nutritional drinks, fruit juice beverages, carbonated beverages and lactic acid beverages; and luxury foods such as dumplings, ice cream, sherbet, gummy and candies. Among these foods and beverages, preferred are beverages and supplements, and more preferred are beverages and capsules.

When the agent for preventing or ameliorating Alzheimer's disease according to the present invention is used in the formulation of a pharmaceutical for internal use, the agent for preventing or ameliorating Alzheimer's disease according to the present invention may be used as it is or combined with any other additive component to prepare a desired form. Specific examples of such pharmaceuticals for internal use include drinks, capsules (soft capsules and hard capsules), tablets, granules, powders, jellies, syrups and liposome preparations. Among these pharmaceuticals for internal use, capsules and drinks are preferred.

When the agent for preventing or ameliorating Alzheimer's disease according to the present invention is in the formulation of a food or beverage or a pharmaceutical for internal use, the content of a ceramide as an active ingredient is not particularly limited as long as it is an effective amount capable of suppressing the accumulation of Aβ in the brain, and may be appropriately set depending on the formulation. The ceramide content is for example 1 to 20% by mass, preferably 3 to 10% by mass, more preferably 6 to 8% by mass.

The agent for preventing or ameliorating Alzheimer's disease according to the present invention can suppress accumulation of Aβ in the brain, and can suppress decrease in cognitive function caused by the accumulation of Aβ, and thus is used for suppressing or delaying the onset of Alzheimer's disease, suppressing the progress of symptoms of Alzheimer's disease, ameliorating the symptoms of Alzheimer's disease, and the like. That is, the subject to whom the agent for preventing or ameliorating Alzheimers disease according to the present invention is to be applied is a person in need of prevention or amelioration of Alzheimer's disease. Examples of the person in need of prevention of Alzheimer's disease include those in need of suppression or delay of the onset of Alzheimer's disease, those who have a tendency to decrease a cognitive function or those suffering from dementia, the elderly, and those who have a tendency to decrease memory or those who have decreased memory. In addition, specific examples of persons in need of amelioration of Alzheimer's disease include those who have developed a symptom of Alzheimer's disease. As one embodiment of the agent for preventing or ameliorating Alzheimer's disease according to the present invention, there is indicated a method involving identifying a person in need of prevention or amelioration of Alzheimer's disease, and administering the agent for preventing or ameliorating Alzheimer's disease according to the present invention to the person.

The amount of the agent for preventing or ameliorating Alzheimer's disease according to the present invention to be applied is not particularly limited, and may be appropriately set depending on the formulation, use, administration target, expected effect, and the like. For example, when the agent for preventing or ameliorating Alzheimers disease according to the present invention is orally taken, the amount of intake is 0.6 to 10 mg, preferably 0.6 to 5 mg per day for an adult in terms of ceramide. The agent for preventing or ameliorating Alzheimer's disease according to the present invention may be administered once or in several doses so that the daily dose falls within the above range.

2. Agent for Maintaining or Ameliorating Memory, Agent for Maintaining or Ameliorating Judgment, and Agent for Maintaining or Ameliorating Cognitive Function Further, the present invention provides an agent for maintaining or ameliorating memory, containing a ceramide as an active ingredient. Specifically, the ceramide can effectively suppress decrease in memory caused by accumulation of Aβ or ameliorate decreased memory caused thereby, and thus can be used for the purpose of maintaining or ameliorating memory. Specifically, the agent for maintaining or ameliorating memory according to the present invention is applied to a person in need of suppression of decrease in memory or in need of amelioration of memory for the purpose of suppressing decrease in memory or ameliorating memory. Those in need of suppression of decrease in memory or in need of amelioration of memory include young people, healthy middle-aged and elderly people, elderly people, people who have a tendency to decrease memory, people who have decreased memory, and people suffering from dementia. In addition, as one embodiment of the agent for maintaining memory according to the present invention, there is indicated a method involving identifying a person in need of suppression of decrease in memory or in need of amelioration of memory, and administering the agent for maintaining memory according to the present invention to the person.

In addition, the present invention provides an agent for maintaining or ameliorating judgment, containing a ceramide as an active ingredient. Specifically, the ceramide can effectively suppress a reduction in judgment caused by accumulation of Aβ or ameliorate a decreased judgment caused thereby, and thus can be used for the purpose of maintaining or ameliorating judgment. Specifically, the agent for maintaining or ameliorating judgment according to the present invention is applied to a person in need of suppression of decrease in judgment or those in need of amelioration of judgment for the purpose of suppressing decrease in judgment or ameliorating judgment. Those in need of suppression of decrease in judgment include young people, healthy middle-aged and elderly people, elderly people, people who have a tendency to decrease judgment, people who have decreased judgment, and people suffering from dementia. In addition, as one embodiment of the agent for maintaining or ameliorating judgment according to the present invention, there is indicated a method involving identifying a person in need of suppression of decrease in judgment or in need of amelioration of judgment, and administering the agent for maintaining judgment according to the present invention to the person.

In addition, the present invention provides an agent for maintaining or ameliorating a cognitive function, containing a ceramide as an active ingredient. Specifically, the ceramide can effectively suppress a reduction in cognitive function caused by accumulation of Aβ, and thus can be used for the purpose of maintaining or ameliorating a cognitive function. Specifically, the agent for maintaining or ameliorating a cognitive function according to the present invention is applied to a person in need of suppression of decrease in cognitive function or those in need of amelioration of a cognitive function for the purpose of suppressing decrease in cognitive function or ameliorating a cognitive function. Those in need of suppression of decrease in cognitive function or in need of amelioration of a cognitive function include people suffering from dementia as well as young people, healthy middle-aged and elderly people, elderly people, and people who have a tendency to decrease a cognitive function. In addition, as one embodiment of the agent for maintaining or ameliorating a cognitive function according to the present invention, there is indicated a method involving identifying a person in need of suppression of decrease in cognitive function or in need of amelioration of a cognitive function, and administering the agent for maintaining a cognitive function according to the present invention to the person.

In the agent for maintaining or ameliorating memory, the agent for maintaining or ameliorating judgement, and the agent for maintaining or ameliorating a cognitive function according to the present invention, the types of the ceramide, other additive components, dosage forms, formulations, doses, etc. to be used are as described in the section "1. Agent for preventing or treating Alzheimer's disease".

EXAMPLES

Next, the present invention will be described in more detail with reference to examples, but is not restricted by these examples.

Example 1

In this experiment, the effect of a glucosylceramide-containing extract on suppression of Aβ accumulation in the brain was verified using Alzheimer's disease model mice.

1. Preparation of Konjak Glucosylceramide-Containing Extract

A konjak glucosylceramide-containing extract was prepared by performing the following extraction treatment, first deodorization treatment, and second deodorization treatment using Konjac flying powder.

(Extraction Treatment)

One (1) kg of Konjac flying powder was charged into a stirring tank, 2 L of ethanol was added thereto, and the mixture was stirred at room temperature for 2 hours. Thereafter, an extract and a residue were separated by filtration. The extract was concentrated by an evaporator to obtain 10.7 g of a brownish waxy concentrate.

(First Deodorization Treatment)

Next, 10.0 g of the obtained waxy concentrate was dissolved in 40.0 mL of ethanol, and then the resultant solution was added into 90 mL of water provided in a glass container having an internal volume of 300 mL with stirring. The mixture was stirred as it was in a dispersed state. After a lapse of 30 minutes, 20.0 g of sodium chloride was added to the container, and the mixture was further stirred for 10 minutes. Thereafter, the stirring was stopped, and the container was transferred onto a hot plate, heated until boiling, and further left still on the hot plate for 1 hour while maintaining the boiling state. Thereafter, the entire contents of the container A were transferred to a separatory funnel, and after confirmation that a yellow transparent aqueous phase appeared at the lower part and a black-brown oil phase appeared at the upper part, the lower aqueous phase was flowed out. To the upper oil phase, 40.0 mL of ethanol was again added. The insoluble matter was removed by filtration with a Buchner funnel, and the filtrate was concentrated to dryness with an evaporator to obtain 7.7 g of a first extract.

(Second Deodorization Treatment)

Next, the obtained first extract was dissolved again in ethanol, and the deodorization treatment was repeated under the same conditions as those for the first deodorization treatment, to obtain 6.3 g of a second extract. When the second extract was analyzed by HPLC, it contained 11% by weight of glucosylceramide. The second extract was used as a konjak glucosylceramide-containing extract in a test which will be described below.

2. Analysis of Effect of Konjak Glucosylceramide-Containing Extract on Intracerebral Aβ Concentration and Amount of Aβ Deposited 2-1. Experimental Method Human APP$^{Sw, Ind}$ gene-transgenic mice (J20, purchased from Jackson Laboratory, USA) were used as Alzheimer's disease model mice. The konjak glucosylceramide-containing extract was dispersed in an aqueous solution of 1% by weight tragacanth gum, and the solution mixture was forcibly administered orally into the stomach of 12-month-old J20 mice. The administration was performed at a dose corresponding to 1 mg glucosylceramide per day for 2 weeks continuously. The control group received only an aqueous solution of 1% by weight tragacanth gum. After continuous administration of the konjak glucosylceramide-containing extract for two weeks, analysis of the intracerebral Aβ concentration by ELISA and immunohistochemical analysis of the amount of Aβ deposited in the brain were performed according to the following methods.

<Analysis of Intracerebral Aβ Concentration by ELISA>

After continuous administration of the konjak glucosylceramide-containing extract for two weeks, the brain tissue was excised and the left-brain hippocampus and cerebral cortex were fractionated. After dissolving the brain tissue with 5 M guanidine hydrochloride, the $Aβ_{1-42}$ concentration was measured using Aβ ELISA (manufactured by Wako Pure Chemical Industries, Ltd.). The measured value was expressed as a concentration per amount (g) of protein in the brain tissue calculated by the BCA method. The $Aβ_{1-42}$ concentration is an average of the values obtained by measuring 10 individuals in the control group and 11 individuals in the konjak glucosylceramide-administered group. Further, the obtained values were subjected to a significance test (**$P<0.01$) by the one-way ANOVA method.

<Immunohistochemical Analysis of Amount of Aβ Deposited in Brain>

After continuous administration of the konjak glucosylceramide-containing extract for 2 weeks, the brain tissue was excised, and the right brain was immersed and fixed in 4% paraformaldehyde overnight to prepare a sagittal paraffin section. The section was immunohistochemically stained with an anti-Aβ antibody (6E10, manufactured by Biolegend). After staining, the hippocampus site was microscopically photographed to measure the number of 6E10 immunopositive spots as the number of Aβ deposition plaques using the image analysis software ImageJ. The measured value was indicated as the number of deposition plaques per area (100 mm$^2$) of the hippocampus site similarly calculated by the ImageJ analysis. The number of deposition plaques is an average of the values obtained by measuring 5 individuals in the control group and 5 individuals in the glucosylceramide-administered group. Further, the obtained values were subjected to a significance test (*$P<0.05$) by the one-way ANOVA method.

2-2. Experimental Results

Figure 1:
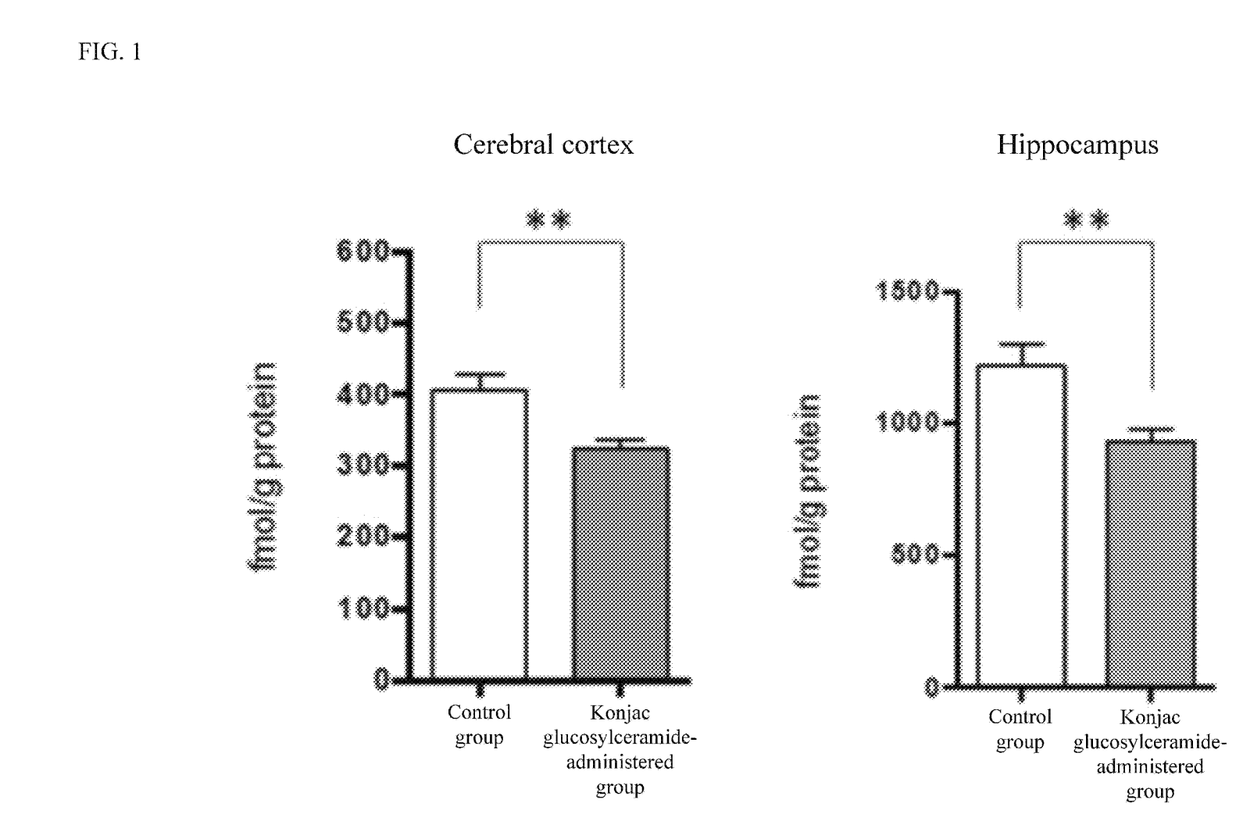
FIG. 1 shows the results of analysis of an intracerebral Aβ concentration after continuous oral administration of a konjak glucosylceramide-containing extract to Alzheimers disease model mice.
Figure 2:
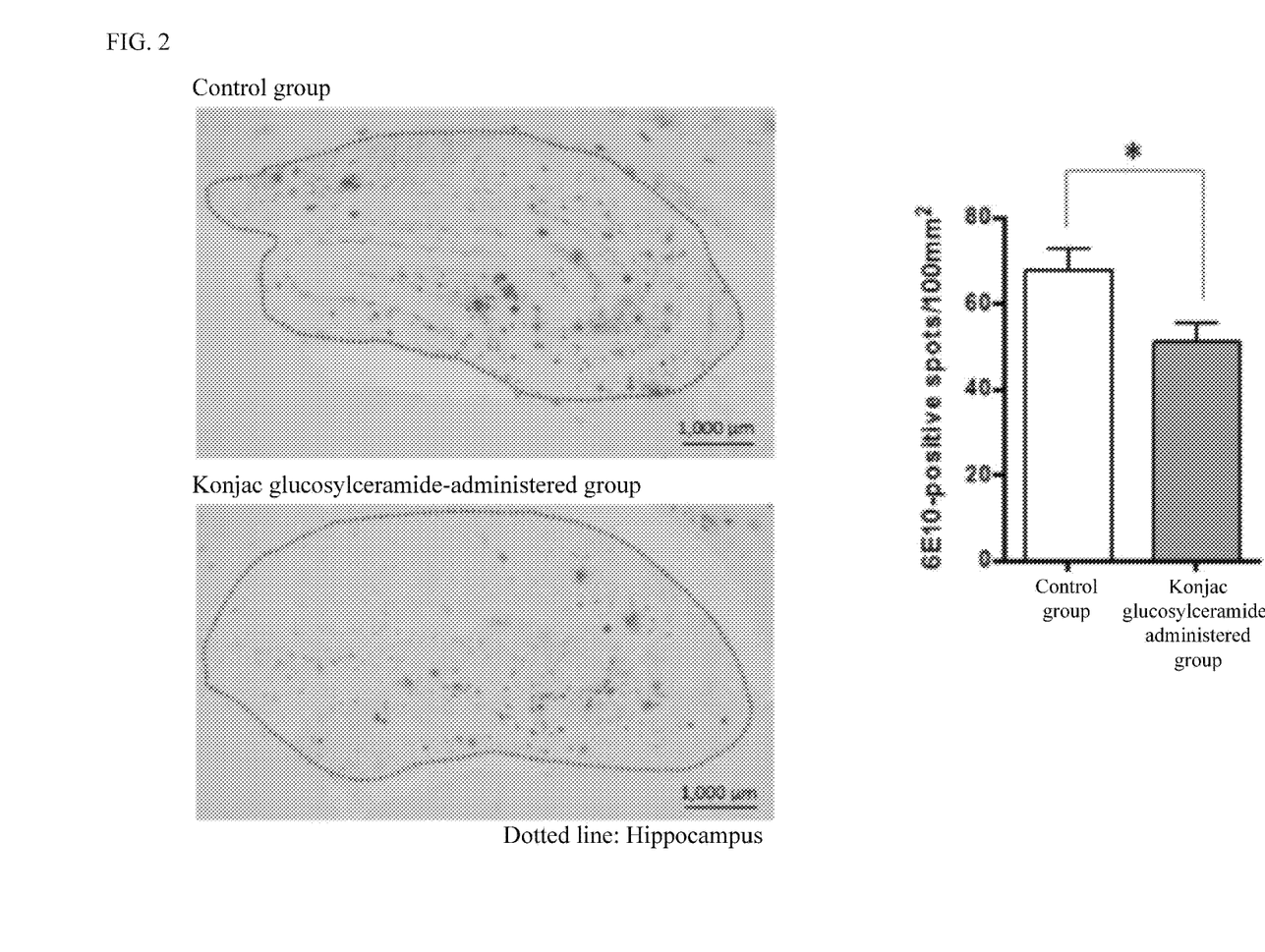
FIG. 2 shows the result (left figure) of immunohistochemical staining of the hippocampus site with an anti-Aβ antibody after continuous oral administration of the konjak glucosylceramide-containing extract to the Alzheimer's disease model mice, and the result (right figure) of determination of Aβ deposition plaques (number of anti-Aβ antibody immunopositive spots) at the hippocampus site.

FIG. 1 shows the results of measurement of the intracerebral Aβ concentration after continuous oral administration of the konjak glucosylceramide-containing extract. FIG. 2 shows the results of immunohistochemical analysis of the amount of Aβ deposited in the brain after the continuous oral administration of the konjak glucosylceramide-containing extract. As a result, it was confirmed that continuous oral administration of the konjak glucosylceramide-containing extract to the Alzheimer's disease model mice could reduce the intracerebral Aβ concentration, and further could suppress the accumulation of Aβ deposition plaques in the brain. From these results, it was revealed that the konjak glucosylceramide-containing extract is effective in preventing or ameliorating Alzheimer's disease.

Example 2

In this experiment, the effect of a purified konjak glucosylceramide on a cognitive function was analyzed using Alzheimer's disease model mice.

1. Preparation of Purified Glucosylceramide

In this experiment. Glucosylceramide, from konjak (product number 170303) purchased from Nagara Science Co., Ltd. was used as a purified konjak glucosylceramide in the following experiment. In addition, as the purified konjak glucosylceramide, a product obtained by removing simple lipids and glycerolipids from the konjak glucosylceramide-containing extract (the second extract) obtained above for purification may be used.

2. Analysis of Effect of Purified Konjak Glucosylceramide on Cognitive Function 2-1. Experimental Method Human APP$^{Sw,\ Ind}$ gene-transgenic mice (J20, purchased from Jackson Laboratory, USA) were used as Alzheimer's disease model mice. The purified konjak glucosylceramide was dispersed in an aqueous solution of 1% by weight tragacanth gum, and the solution mixture was forcibly administered orally into the stomach of 12-month-old J20 mice. The purified konjak glucosylceramide was administered at a dose of 1 mg/day/head for 2 weeks continuously. The control group received only an aqueous solution of 1% by weight tragacanth gum. After continuous administration of the purified konjak glucosylceramide for 2 weeks, working memory analysis using a Y-maze was performed according to the following method. The working memory analysis using the Y-maze was also performed on normal mice (C57BL/6 strain, purchased from Japan SLC, Inc., 12 months old).

<Analysis of Cognitive Function by Y-Maze>

After continuous administration of the purified konjak glucosylceramide for 2 weeks, a Y-maze test was performed to evaluate short-term memory by means of the spontaneous alternation behavior. In the Y-maze test, a Y-maze (manufactured by Panlab) was used in which three arms having an arm length of 35 cm, a wall height of 11 cm, a floor width of 3 cm, an upper width of 10 cm were connected at an angle of 120 degrees each. The mouse was placed at the tip of any one of the arms in the Y-maze, allowed to freely explore the maze for 8 minutes, and the arm to which the mouse moved was recorded in order. The number of times the mouse moved to each arm within the measurement time was counted, and this value was defined as the total number of entries. In addition, a combination in which three different arms were successively selected was examined, and this number was defined as the number of spontaneous alternation behaviors. The spontaneous alternation behavior change rate was determined according to the following formula. The higher the spontaneous alternation behavior change rate was, the more the short-term memory was held.

Spontaneous alteration behavior change rate (%)={number of spontaneous alteration behaviors/(total number of entries−2)}×100[Mathematical Formula 1]

This experiment was conducted with 7 mice in the purified konjak glucosylceramide-administered group, 7 mice in the control group, and 5 mice in the normal mouse group. In addition, a significance test between the control group and the purified konjak glucosylceramide-administered group was performed through a Student t-test for the spontaneous alternation behavior change rate.

2-2. Experimental Results

Figure 3:
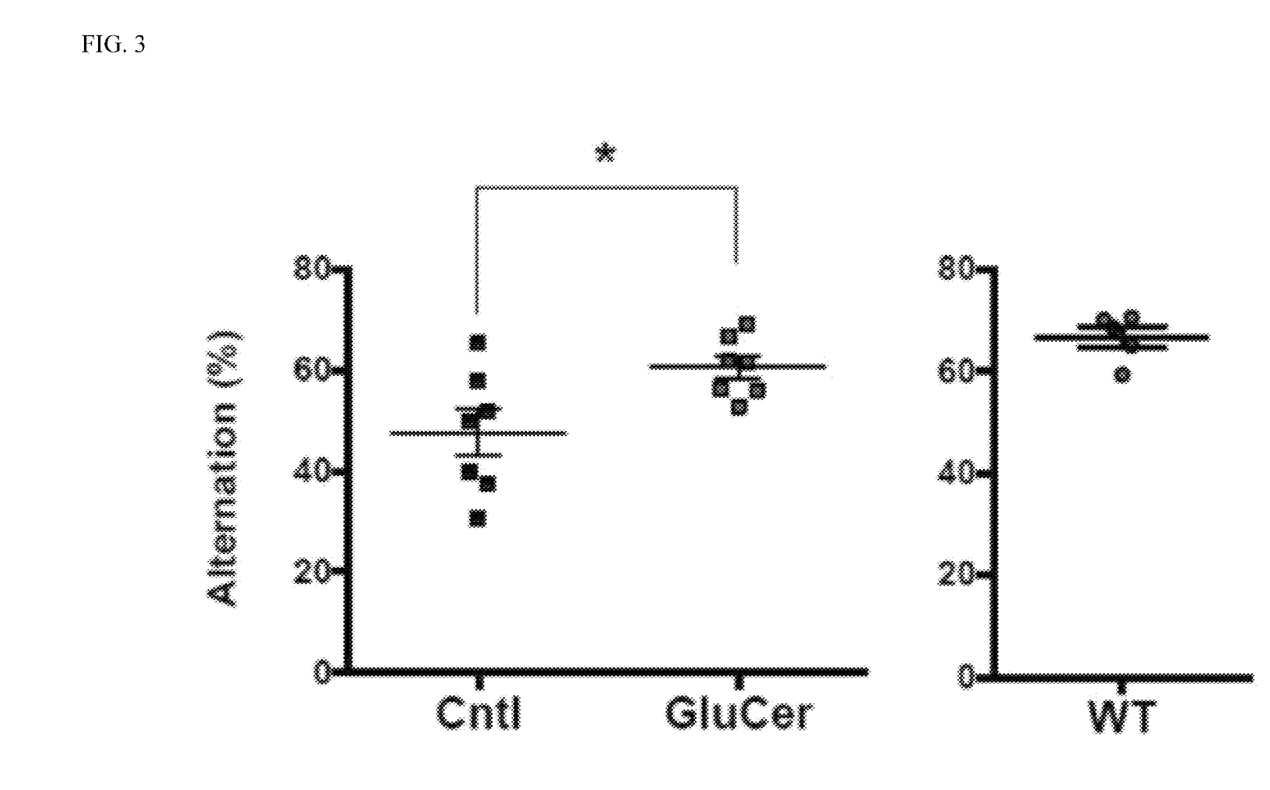
FIG. 3 shows the results of verifying a cognitive function through a Y-maze test after continuous oral administration of a purified glucosylceramide to Alzheimer's disease model mice.

FIG. 3 shows the results of analysis of the cognitive function after continuous oral administration of the purified konjak glucosylceramide. In FIG. 3, "Cntl" represents the control group, "GluCer" represents the purified konjak glucosylceramide-administered group, and "WT" represents the normal mouse group. FIG. 3 plots the value of each individual for the spontaneous alternation behavior change rate (Alternation), and also indicates the average±standard error of each group. As a result, the mice to which the purified konjak glucosylceramide was orally administered showed an improved spontaneous alternation behavior change rate in the Y-maze test, which verified that the purified konjak glucosylceramide not only had the effect of suppressing the decrease in cognitive function, but also had the effect of improving the spontaneous alternation behavior change rate, which was once decreased, and recovering it back to a level close to the cognitive function level of the normal mice.

The invention claimed is:

1. A method for ameliorating cognitive function in Alzheimer's disease to a person in need of amelioration of Alzheimer's disease and cognitive function, comprising a step of administering an effective amount of a ceramide to the person,
   wherein the ceramide is derived from tuber of *Amorphophallus konjac* and wherein the ceramide comprises a glucosylceramide of 4,8-sphingadienine.

2. The method according to claim 1, wherein the ceramide is in a form of food or beverage.

3. The method according to claim 1, wherein the ceramide is in a form of pharmaceutical.

4. The method according to claim 1, wherein a composition containing the ceramide with a content of 1 to 20% by mass is administered.

5. The method according to claim 1, wherein a dosage of the ceramide is 0.6 to 10 mg per day.

6. The method according to claim 1, wherein the glucosylceramide is a glucosylceramide of trans-4, cis-8-sphingadienine or trans-4-trans-8-sphingadienine.

7. The method according to claim 1, wherein a composition containing the ceramide with a content of 1 to 20% by mass is administered, and
   wherein a dosage of the ceramide is 0.6 to 10 mg per day.

* * * * *